United States Patent
Burruano et al.

(10) Patent No.: US 6,953,775 B2
(45) Date of Patent: Oct. 11, 2005

(54) COMPOSITION FOR SYNTHETIC CERVICAL MUCUS FORMULATION

(76) Inventors: Brid T. Burruano, 600 S. Forty-third St., Philadelphia, PA (US) 19104-4495; Roger L. Schnaare, 600 S. Forty-third St., Philadelphia, PA (US) 19104-4495

( * ) Notice: Subject to any disclaimer, the term of this patent is extended or adjusted under 35 U.S.C. 154(b) by 142 days.

(21) Appl. No.: 10/268,590

(22) Filed: Oct. 10, 2002

(65) Prior Publication Data

US 2004/0072730 A1 Apr. 15, 2004

(51) Int. Cl.[7] .............................................. A61K 38/02
(52) U.S. Cl. ............................................... 514/8; 514/2
(58) Field of Search ........................... 514/8, 781, 782, 514/769, 2

(56) References Cited

U.S. PATENT DOCUMENTS

| | | | | |
|---|---|---|---|---|
| 4,438,100 A | * | 3/1984 | Balslev et al. | 424/537 |
| 5,492,937 A | * | 2/1996 | Bogentoft et al. | 514/781 |
| 5,736,322 A | * | 4/1998 | Goldstein | 435/5 |

OTHER PUBLICATIONS http://www.academy.org.uk/pharmacy/benzal.htm.*
Brurauno BT; Schnaare RL, Malamud D. Synthetic cervical mucus formulation. Contraception (2002) Aug. 66(2), pp. 137–140. Available Online Aug. 25, 2002.*

* cited by examiner

*Primary Examiner*—Bruce R. Campell
*Assistant Examiner*—Andrew D. Kosar
(74) *Attorney, Agent, or Firm*—Reed Smith LLP

(57) ABSTRACT

The present invention is a composition for a synthetic mucus formulation with viscosity, spinnbarkeit, and pH comparable to that reported for human cervical mucus.

12 Claims, No Drawings

COMPOSITION FOR SYNTHETIC CERVICAL MUCUS FORMULATION

FIELD OF THE INVENTION

The present invention relates to compositions and methods for creating a synthetic mucus formulation with viscosity, spinnbarkeit, and pH comparable to that reported for human cervical mucus. The composition comprises effective amounts of viscosity increasing agents and glycoproteins. More particularly, the effective viscosity increasing agents and glycoproteins are guar gum and dried porcin gastric mucin (type III), respectively.

BACKGROUND OF THE INVENTION

Fresh cervical mucus, human or otherwise, is difficult to obtain in large quantities and degrades rapidly once collected from its source. The testing of vaginal pharmaceuticals, drug delivery methods and fertility aids, for example, depend on a readily obtainable, time stable supply of cervical mucus. For this reason, there is a great need for the development of a synthetic mucus formulation with characteristics similar to that of fresh human cervical mucus.

Cervical mucus is produced by the cervical glands in the cervix. Cervical mucus acts as a biological filter, preventing the influx of vaginal bacterial flora and enhancing sperm survival. Cervical mucus is an essential element to conception and its physical properties change predictably and cyclically during the menstrual cycle. It is produced in response to the action of the hormones estrogen and progesterone. During the first half of the cycle, before mid-cycle ovulation, as estrogenic hormone release increases, the cervical mucus produced is watery, copious, clear and stretchy. After ovulation, the quality of the mucus changes in response to increased levels of progesterone becoming thicker, sticker and reduced in amount as the cycle ends.

Mid-cycle cervical mucus represents the best opportunity for the successful introduction of sperm, pharmaceuticals, and similar applications designed to penetrate the uterine system due to a decrease in mucus viscoelasticity. The composition of mid-cycle cervical mucus contains about 1% to 1.5% electrolytes, about 0.5% to 1.0% proteins, about 0.5% to 1.0% lipids, about 0.5% to 5% glycoproteins, and about 95% water. The characteristics of mid-cycle cervical mucus include a pH of about 7.4 and a viscosity of about 2,840 to 10,000 cP.

Mucins are a family of glycoproteins with particularly high molecular weight. Mucins are secreted or expressed by goblet and nongoblet epithelial cells at many body surfaces, including the eyes, pancreatic ducts, gallbladder, prostate and mainly, respiratory, gastrointestinal and female reproductive tracts. Mucins are capable of forming viscous and highly hydrated gels, such as mucus, and thereby act as lubricants or protecants in cavities of the body or on body surfaces. At least nine distinct mucin genes have been identified in the human body: MUC1, 2, 3, 4, MUC5AC, MUC5B, MUC6, 7 and 8.

Previous to the present invention, mucus substitutes known in the art included hen egg white, guar gum, hyaluronic acid, acrylimide and polyacrilimide, albumin tyrode solution, and gum tragacanth. Most of the aforementioned substitutes are used only for sperm penetration testing. This limitation in use results because each previously known substitute lacks a glycoprotein fraction representative of fresh cervical mucus.

A synthetic cervical mucus can be used to test the performance of existing and new vaginal product formulations such as fertility drugs, contraceptives and drugs for the treatment of vaginal infections, as well as for other purposes.

Prior patents provide no teaching concerning the use of combinations of viscosity increasing agents and glycoproteins as effective in creating a gel formulation with viscosity, spinnbarkeit, and pH properties comparable to that reported for human cervical mucus.

It is well known in the art that viscosity increasing agents are especially useful in forming gels when crosslinking agents are used to assist in forming gels at low concentrations of viscosity increasing agents and to form gels having properties not obtainable by their use alone. A well known crosslinking agent for viscosity increasing agents, specifically for use with guar gum, is the borate ion which acts as a crosslinking agent with a hydrated viscosity increasing agents to form cohesive structural gels.

SUMMARY OF THE INVENTION

The present invention includes a composition comprising an effective amount of one or more viscosity increasing agents and an effective amount of one or more glycoproteins having viscosity, spinnbarkeit, and pH comparable to that reported for human cervical mucus. The viscosity increasing agents include but are not limited to guar gum, locust bean gum, xanthan gum, tara gum, fenugreek gum, and mesquite gum. The glycoproteins include, but are not limited to, porcine gastric mucin (type II), porcine gastric mucin (type III), bovine submaxillary glands mucin (type I), and bovine submaxillary glands mucin (type I-S). Other useful glycoproteins include MUC1, MUC 2, MUC 3, MUC 4, MUC5AC, MUC5B, MUC6, MUC7 and MUC8.

Another embodiment of the present invention includes a composition comprising guar gum, glycoproteins, methylparaben, propylparaben and imidurea, and 0.1 M pH 7.4 potassium phosphate buffer. Examples of guar gum sources include, but are not limited to, Hercules guar gum and Sigma guar gum. Examples of glycoproteins include, but are not limited to, porcine gastric mucin (type II), porcine gastric mucin (type III), bovine submaxillary glands mucin (type I), and bovine submaxillary glands mucin (type I-S).

Another embodiment of the present invention includes a method of hydrating the viscosity increasing agents by diluting a preservative into about 90 percent water by weight, mixing for five minutes at a high speed, slowly adding the viscosity increasing agent, adding an effective amount of glycoproteins, adding a solution of buffers and preservatives, and adding a 0.1 M sodium borate solution.

An additional embodiment of the present invention includes a method of hydrating the viscosity increasing agents by diluting the viscosity increasing agent, glycoproteins, preservatives and buffers into 100 percent water by weight, mixing for 10 minutes, and adding a 0.1 M sodium borate solution.

DETAILED DESCRIPTION OF THE INVENTION

The present invention includes a composition comprising an effective amount of one or more viscosity increasing agents and an effective amount of glycoproteins having viscosity, spinnbarkeit, and pH comparable to that reported for human cervical mucous.

What is meant by "an effective amount" refers to an amount of viscosity increasing agents and glycoproteins sufficient to obtain a viscosity, spinnbarkeit, and pH comparable to that reported for human cervical mucous.

What is meant by the term "preservatives" includes compounds capable of preserving the viscosity increasing agents and mucin agents, preferably in the minimum amount required to preserve the viscosity increasing agents and glycoproteins, preferably about 0.15% methylparaben, about 0.02% propylparaben, and about 0.30% imidurea.

"Viscosity increasing agents" refers to compounds capable of increasing viscosity, preferably in the minimum amount required to effect a viscosity of about 2,840 to 10,000 cP. Preferable viscosity increasing agents include cellulose derivatives and gums. Suitable gums include, guar gum, locust bean gum, xanthan gum, tara gum, fenugreek gum, and mesquite gum.

Many formulations have been made in laboratory experiments to show the various embodiments of the invention and the ingredients used.

All percentages are weight percentages unless otherwise noted.

EXAMPLE 1

| Weight % | |
|---|---|
| 1.00 | Guar gum |
| 0.50 | Porcine gastric mucin (type III) |
| 0.28 | Potassium phosphate, monobasic |
| 1.36 | Potassium phosphate, dibasic |
| 0.55 | DMDM Hydantoin |
| 0.10 | Sodium azide |
| 96.21 | Water |

200 gm of water were weighed into a blender beaker and set to run. Guar gum was slowly added and mixed for at least ten minutes. The mucin, phosphates and preservatives were dissolved in the remaining water and then added to the blender. The mixture was poured into a container and 0.5 ml 0.1 M sodium borate solution was added. The container and its contents were then well shaken.

EXAMPLE 2

| Weight % | |
|---|---|
| 1.00 | Guar gum |
| 0.50 | Porcine gastric mucin (type III) |
| 1.36 | Potassium phosphate, dibasic |
| 0.28 | Potassium phosphate, monobasic |
| 0.02 | Proylparaben |
| 0.15 | Methylparaben |
| 96.69 | Water |

EXAMPLE 3

| Weight % | |
|---|---|
| 1.00 | Guar gum |
| 1.00 | Porcine gastric mucin (type III) |
| 1.36 | Potassium phosphate, dibasic |
| 0.28 | Potassium phosphate, monobasic |
| 0.02 | Proylparaben |
| 0.15 | Methylparaben |
| 96.19 | Water |

EXAMPLE 4

| Weight % | |
|---|---|
| 1.00 | Guar gum |
| 0.50 | Porcine gastric mucin (type III) |
| 1.74 | Potassium phosphate, dibasic |
| 0.09 | Potassium phosphate, monobasic |
| 96.67 | Water |

EXAMPLE 5

| Weight % | |
|---|---|
| 1.00 | Guar gum |
| 0.10 | Porcine gastric mucin (type III) |
| 1.57 | Potassium phosphate, dibasic |
| 0.26 | Potassium phosphate, monobasic |
| 0.02 | Proylparaben |
| 0.15 | Methylparaben |
| 96.90 | Water |

It is understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A synthetic cervical mucus composition, comprising:
   an effective amount of one or more viscosity increasing agents; and
   an effective amount of glycoproteins;
   wherein the composition has a viscosity of about 2,840 to about 10,000 cP.
2. The composition of claim 1 wherein the glycoproteins comprise one or more mucins.
3. The composition of claim 2 wherein the mucins comprise one or more of the group consisting of porcine gastric mucin (type II), porcine gastric mucin (type III), bovine submaxillary glands mucin (type I), and bovine submaxillary glands mucin (type I-S).
4. The composition of claim 1 wherein the glycoproteins comprise about 0.01 to about 1.00 percent of the composition.
5. The composition of claim 1 further comprising one or more preservatives.
6. The composition of claim 5 wherein the preservatives comprise one or more of the group consisting of methylparaben, propylparaben, sodium azide, DMDM hydantoin and imidurea.
7. The composition of claim 5 wherein the preservatives comprise about 0.25 to about 1.00 percent of the composition.
8. The composition of claim 1 further comprising one or more buffers.
9. The composition of claim 8 wherein the buffers comprise one or more of the group consisting of dibasic potassium phosphate and monobasic potassium phosphate.
10. The composition of claim 8 wherein the buffers comprise about 1.15 to about 2.00 percent of the composition.
11. The composition of claim 1 wherein the pH of the synthetic mucus composition is about 6.5 to about 8.5.
12. The composition of claim 1 wherein the viscosity increasing agents comprise one or more of the group consisting of cellulose derivatives, guar gum, hyaluronic acid, acrylamide and polyacrylamide.

* * * * *